(12) United States Patent
Selvaganapathy et al.

(10) Patent No.: US 9,841,381 B2
(45) Date of Patent: Dec. 12, 2017

(54) TEMPERATURE CHANGE INDICATOR AND METHODS OF MAKING THE SAME

(71) Applicant: McMaster University, Hamilton (CA)

(72) Inventors: Ponnambalam Ravi Selvaganapathy, Dundas (CA); Wen-I Wu, Ancaster (CA)

(73) Assignee: MCMASTER UNIVERSITY, Hamilton (CA)

( * ) Notice: Subject to any disclaimer, the term of this patent is extended or adjusted under 35 U.S.C. 154(b) by 0 days.

(21) Appl. No.: 15/027,644

(22) PCT Filed: Oct. 10, 2013

(86) PCT No.: PCT/CA2013/050764
§ 371 (c)(1),
(2) Date: Apr. 6, 2016

(87) PCT Pub. No.: WO2015/051437
PCT Pub. Date: Apr. 16, 2015

(65) Prior Publication Data
US 2016/0258873 A1    Sep. 8, 2016

(51) Int. Cl.
*G01N 21/78* (2006.01)
*G01K 11/16* (2006.01)
*G01K 11/18* (2006.01)

(52) U.S. Cl.
CPC ............. *G01N 21/78* (2013.01); *G01K 11/16* (2013.01); *G01K 11/18* (2013.01)

(58) Field of Classification Search
CPC .................. G01N 21/78; G01N 31/229; Y10T 428/24942; G01K 11/06; G01K 11/16; G01K 11/18; G01K 3/04; G01K 1/02
(Continued)

(56) References Cited

U.S. PATENT DOCUMENTS 5,053,339 A * 10/1991 Patel .................... G01N 31/229
116/206
5,667,303 A *  9/1997 Arens ...................... G01K 3/04
116/219
(Continued)

FOREIGN PATENT DOCUMENTS

WO         2012050824 A1     4/2012

OTHER PUBLICATIONS

"Cumulative Heat Indicators," accessed at https://web.archive.org/web/20110919110500/http://www.temptimecorp.           com/PublicPages/Cumulative-Heat-Indicators.aspx, (2009) accessed on Mar. 30, 2016, 1 Page.
(Continued)

*Primary Examiner* — Ruiyun Zhang
(74) *Attorney, Agent, or Firm* — Maschoff Brennan

(57) ABSTRACT

Sensors including thermal load sensors and chemical or biological load sensors, and methods of making the sensors, are disclosed. The sensors may include a solid polymeric matrix and at least one organic indicating material encapsulated within the solid polymeric matrix, wherein the organic indicating material is configured to diffuse into the solid polymeric matrix at a phase transition temperature of the organic indicating material, and wherein an extent of diffusion indicates a target load on the sensor. The target load may, for example, be a thermal load, or a chemical or biological load.

20 Claims, 3 Drawing Sheets

(58) Field of Classification Search
USPC ......... 374/106, 160–162; 116/216, 217, 219, 116/206, 207; 436/2
See application file for complete search history.

(56) References Cited

U.S. PATENT DOCUMENTS

| | | | |
|---|---|---|---|
| 6,435,128 B2 * | 8/2002 | Qiu | .......................... G01K 3/04 |
| | | | 116/207 |
| 7,063,041 B2 | 6/2006 | Odashiro | |
| 8,066,432 B2 | 11/2011 | Yang et al. | |
| 2014/0044609 A1 | 2/2014 | Prusik et al. | |

OTHER PUBLICATIONS

"Timestrip," accessed at https://web.archive.org/web/20131006200845/http://www.timestrip.com/, (2012) accessed on Mar. 30, 2016, 1 Page.

"Time temperature indicator," accessed at https://web.archive.org/web/20130515093612/http://en.wikipedia.org/wiki/Time_temperature_indicator, last modified on Mar. 8, 2013, 2 Pages.

Frost, L. J. and Reich, M. R., "Vaccine Vial Monitors: Access to Devices," in How Do Good Health Technologies Get to Poor People in Poor Countries, Chapter 7, pp. 142-166 (May 2008).

International Search Report and Written Opinion for International Application No. PCT/CA2013/050764, dated Jul. 8, 2014 (4 pages).

Lerchner, J., et al., "Calorimetric detection of volatile organic compounds," Sensors and Actuators B: vol. 70, Issues 1-3, pp. 57-66 (Nov. 1, 2000).

Vermeir, S., et al., "Microplate Differential Calorimetric Biosensor for Ascorbic Acid Analysis in Food and Pharmaceuticals," Analytical Chemistry, vol. 79, Issue 16, pp. 6119-6127 (Aug. 15, 2007).

* cited by examiner

TEMPERATURE CHANGE INDICATOR AND METHODS OF MAKING THE SAME

CROSS-REFERENCE TO RELATED APPLICATION

The present application is a U.S. National Stage Application under 35 U.S.C. §371 of International Application No. PCT/CA2013/050764, filed on Oct. 10, 2013, the entire contents of which are incorporated herein by reference.

BACKGROUND

Transportation of various goods from their original location, such as warehouses, processing plants, or pharmaceutical companies, to their intended destination, such as supermarkets or dispensaries, can expose these goods to various thermal loads. Thermal loads such as extremely high temperatures or moderately high temperatures for short or long durations can result in spoilage or loss of efficacy of the goods. Goods such as frozen foods, beverages, medical drugs, and vaccines need to be protected from exposure to high temperatures. Thus, there is demand for proper monitoring of goods to ensure proper temperature control during transportation.

Electronic systems that log the temperature over time can be used, but such systems are expensive and require active monitoring, data storage, calibration, and training for the intended user. A simple, cost-effective system that measures and reports thermal history, including exposure temperature and the duration of exposure would be beneficial.

SUMMARY

In an embodiment, a method of making a thermal load sensor may include encapsulating at least one organic indicating material in a solid polymeric matrix, wherein the organic indicating material may diffuse into the solid polymeric matrix at a phase transition temperature of the organic indicating material, and wherein an extent of diffusion may indicate a thermal load on the sensor. In some embodiments, the encapsulating may include adding a first curable polymeric material into a container, curing the first curable polymeric material to form a first cured polymeric material, forming an organic indicating material into a shape smaller than the first cured polymeric material, placing the organic indicating material on the first cured polymeric material, applying a second curable polymeric material on the organic indicating material and the first cured polymeric material so as to encapsulate the organic indicating material, and curing the second curable polymeric material to form a second cured polymeric material.

In an embodiment, a method of fabricating a chemical or biological load sensor may include encapsulating at least one organic indicating material in a solid polymeric matrix, wherein the organic indicating material may diffuse into the solid polymeric matrix when contacted with a target material that triggers an exothermic reaction to heat the organic indicating material to a phase transition temperature, and wherein an extent of diffusion may indicate a chemical or biological load on the sensor. In some embodiments, the encapsulating may include adding a first curable polymeric material into a container, curing the first curable polymeric material to form a first cured polymeric material, forming an organic indicating material into a shape smaller than the first cured polymeric material, placing the organic indicating material on the first cured polymeric material, applying a second curable polymeric material on the organic indicating material and the first cured polymeric material so as to encapsulate the organic indicating material, and curing the second curable polymeric material to form a second cured polymeric material.

In an embodiment, a thermal load sensor may include a solid polymeric matrix, and at least one organic indicating material encapsulated within the solid polymeric matrix, wherein the organic indicating material may diffuse into the solid polymeric matrix at a phase transition temperature of the organic indicating material, and wherein an extent of diffusion may indicate a thermal load on the sensor.

In an embodiment, a chemical or biological load sensor may include a solid polymeric matrix, and at least one organic indicating material encapsulated within the solid polymeric matrix, wherein the organic indicating material may diffuse into the solid polymeric matrix when contacted with a target material that triggers an exothermic reaction to heat the organic indicating material to a phase transition temperature, and wherein an extent of diffusion may indicate a chemical or biological load on the sensor.

In a further embodiment, an article of manufacture may include a sensor having a solid polymeric matrix and at least one organic indicating material encapsulated within the solid polymeric matrix, wherein the organic indicating material may diffuse into the solid polymeric matrix at a phase transition temperature of the organic indicating material, and wherein an extent of the diffusion may indicate a target load on the sensor.

In an embodiment, a method of detecting a thermal load may include providing at least one thermal load sensor having a solid polymeric matrix, and at least one organic indicating material encapsulated within the solid polymeric matrix, and determining the thermal load from the at least one thermal load sensor based on an amount of diffusion of the organic indicating material into the solid polymeric matrix.

In an embodiment, a method of detecting a chemical or biological load may include providing at least one chemical or biological load sensor having a solid polymeric matrix, and at least one organic indicating material encapsulated within the solid polymeric matrix; and detecting a chemical or biological load from the at least one chemical or biological load sensor based on an amount of diffusion of the organic indicating material into the solid polymeric matrix.

DETAILED DESCRIPTION

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art.

Nothing in this disclosure is to be construed as an admission that the embodiments described in this disclosure are not entitled to antedate such disclosure by virtue of prior invention. As used in this document, the term "comprising" means "including, but not limited to."

The following terms shall have, for the purposes of this application, the respective meanings set forth below.

A "load" as used herein refers to any condition to which an object or material is subjected, caused an effect on the object or material. A "thermal load" refers to any temperature that causes an effect on an object or material. A "chemical load" refers to any chemical that causes an effect on an object or material. A "biological load" refers to any biological substance that causes an effect on an object or material.

A "sensor" refers to any device or apparatus that detects or measures a physical, biological, or chemical property, and records, indicates, or otherwise responds to the physical, biological, or chemical property. For example, a thermal load sensor is a sensor that detects a change in temperature and indicates this change in temperature by any method of reporting, such as a color change on the sensor.

An "organic indicating material" is any organic material that responds to a thermal, chemical, or biological load. A "curable polymeric material" is any material that is polymer based and after initiating cross-linking of polymer chains within the material results in a different density of the material.

A "solid polymeric matrix" is a material in a solid state that is a polymer based in which other materials or objects are embedded.

Figure 1:
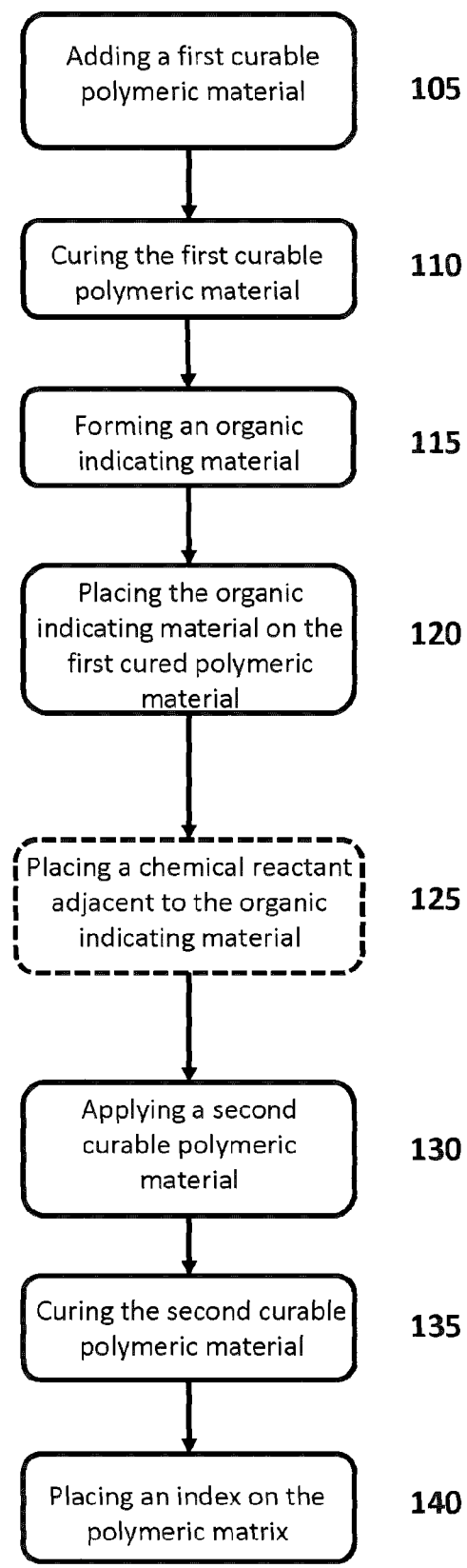
FIG. 1 depicts a flowchart of an illustrative method of making a load sensor according to an embodiment.

FIG. 1 depicts a flowchart of an illustrative method of fabricating a load sensor according to an embodiment. In an embodiment, the load sensor may be a thermal load sensor. In an embodiment, the load sensor may be a chemical load sensor. In an embodiment, the load sensor may be a biological load sensor. In an embodiment, the sensor may be one or more of a thermal load sensor, a chemical load sensor and a biological load sensor.

In some embodiments, a load sensor may be fabricated by encapsulating at least one organic indicating material in a solid polymeric matrix. In some embodiments, where the sensor is a thermal load sensor, the organic indicating material may diffuse into the solid polymeric matrix at or above a phase transition temperature of the organic indicating material. In other embodiments, where the sensor is a chemical or biological load sensor, the organic indicating material may diffuse into the solid polymeric matrix when contacted with a target material that triggers an exothermic reaction to heat the organic indicating material to a phase transition temperature. The extent of diffusion may indicate a thermal, chemical, or biological load on the sensor. In some embodiments, the thermal, biological, or chemical load may be indicated as a change in the solid polymeric matrix from transparent to at least substantially opaque. In other embodiments, the thermal, chemical, or biological load may be indicated as any change in color of the solid polymeric matrix. The change in color may be any color within the visible spectrum and may change to a lighter or darker shade depending on the diffusion of the organic indicating material. In some embodiments, the thermal load may include an exposure time. In other embodiments, the thermal load may include an exposure temperature. In further embodiments, the thermal load may include both an exposure time and an exposure temperature. In some embodiments, the chemical or biological load may include an exposure time, concentration of the target material, type of target material, or any combination thereof.

In some embodiments, the phase transition temperature may be about 15° C. to about 350° C. For example, the phase transition temperature may be about 15° C., about 30° C., about 40° C., about 50° C., about 60° C., about 70° C., about 80° C., about 90° C., about 100° C., about 125° C., about 150° C., about 175° C., about 200° C., about 225° C., about 250° C., about 275° C., about 300° C., about 325° C., about 350° C., or a range between any of these values (including endpoints). In some embodiments, the phase transition temperature may be about 30° C. to about 300° C.

In some embodiments, the organic indicating material may be a hydrophobic material that undergoes a phase transition from a solid to a liquid at the phase transition temperature. In some embodiments, the organic indicating material may have a carbon chain with at least 2 carbon atoms. In other embodiments, the organic indicating material may have a carbon chain with at least 2 carbon atoms to at least 100 carbon atoms. For example, the organic indicating material may have a carbon chain with at least 2 carbon atoms, at least 3 carbon atoms, at least 4 carbon atoms, at least 5 carbon atoms, at least 6 carbon atoms, at least 7 carbon atoms, at least 8 carbon atoms, at least 9 carbon atoms, at least 10 carbon atoms, at least 15 carbon atoms, at least 20 carbon atoms, at least 50 carbon atoms, at least 100 carbon atoms, or any range between any two of these values. In further embodiments, the organic indicating material may be a paraffin having at least 2 carbon atoms to at least 100 carbon atoms. In some embodiments, the organic indicating material may be a paraffin having at least 9 carbon atoms. The organic indicating material may be a paraffin wax.

In some embodiments, the solid polymeric matrix may include a first curable polymeric material. In some embodiments, the solid polymeric matrix may further include a second curable polymeric material. In some embodiments, at least one of the first curable polymeric material and the second curable polymeric material may be a hydrophobic elastomeric material. In other embodiments, at least one of the first curable polymeric material and the second curable polymeric material may be polycarbonate, an acrylate polymer, polyurethane, a siloxane-based polymer, and/or a co-polymer of any of the foregoing. In further embodiments, at least one of the first curable polymeric material and the second curable polymeric material may be polydimethylsiloxane.

In an embodiment where the sensor is a chemical or biological load sensor, the target material may be a pesticide, a hormone, a microorganism, a dye composition, a polymer, a hydrogen gas, an acid, a base, a volatile organic compound, or any combination thereof. The acid may include, for example, acetic acid, benzoic acid, carbonic acid, formic acid, hydrochloric acid, hydrogen sulfide, nitric acid, phosphoric acid, sulfuric acid, or any combination thereof. The base, for example, may include ammonium hydroxide, calcium hydroxide, potassium hydroxide, sodium hydroxide, or any combination thereof.

A method of making a load sensor according to an embodiment is shown in FIG. 1. Referring to FIG. 1, a first curable polymeric material may be added 105 into a container. The container may be of a particular shape or volume, such as a cube, a cuboid, a square-based pyramid, a triangular-based pyramid, a triangular prism, a hexagonal prism, a cone, a sphere, a cylinder, or any combination thereof. The first curable polymeric material may be added 105 to the container by pouring the material, adding the material dropwise, dispensing the material, or the like.

The first curable polymeric material may be cured 110. In some embodiments, the curing 110 of the first curable polymeric material may be performed by chemical additives, ultraviolet radiation, electron beam, heat, or any combination thereof. In other embodiments, the curing 110 of the first curable polymeric material may be performed via multiple steps to achieve various levels of curing of the first curable polymeric material. In further embodiments, the curing 110 of the first curable polymeric material may be step-curing, ramp curing, single intensity curing, or any other method of curing. In some embodiments, the curing 110 of the first curable polymeric material may be in the presence of oxygen. In other embodiments, the first curable polymeric material may be cured 110 in the absence of oxygen. In some embodiments, the first curable polymeric material may be cured 110 at a temperature of about 20° C. to about 350° C. For example, the material may be cured 110 at a temperature of about 20° C., about 40° C., about 60° C., about 80° C., about 100° C., about 120° C., about 140° C., about 160° C., about 180° C., about 200° C., about 250° C., about 300° C., about 350° C., or at temperatures within a range between any of these values (including endpoints). In some embodiments, the first curable polymeric material may be cured 110 to a flexible state.

The organic indicating material may be formed 115. In some embodiments, a plurality of organic indicating materials may be formed 115. In some embodiments, the organic indicating material may be formed 115 by constructing the organic indicating material into a cube, a cuboid, a square-based pyramid, a triangular-based pyramid, a triangular prism, a hexagonal prism, a cone, a sphere, a cylinder, or a combination thereof. In other embodiments, forming 115 the organic indicating material into a shape may include thermoforming the organic indicating material in a chamber. In other embodiments, forming 115 the organic indicating material into a shape may include mechanically cutting a solid phase organic indicating material.

In other embodiments, forming 115 the organic indicating material may include constructing the organic indicating material into a cylinder. In other embodiments, the cylinder may have a cross-sectional diameter of about 1 millimeter to about 30 millimeters. For example, the cylinder may have a cross-sectional diameter of about 1 millimeter, about 2 millimeters, about 3 millimeters, about 4 millimeters, about 5 millimeters, about 6 millimeters, about 7 millimeters, about 8 millimeters, about 9 millimeters, about 10 millimeters, about 20 millimeters, about 30 millimeters, or a range between any of these values (including endpoints). In other embodiments, the cylinder may have a height of about 0.5 millimeters to about 20 millimeters. For example, the cylinder may have a height of about 0.5 millimeters, about 1 millimeter, about 2 millimeters, about 3 millimeters, about 4 millimeters, about 5 millimeters, about 10 millimeters, about 20 millimeters, or a range between any of these values (including endpoints). In one embodiment, the cylinder may have a diameter of about 1 millimeter to about 10 millimeters and a height of about 0.5 millimeters to about 5 millimeters. In a particular embodiment, the cylinder may have a diameter of about 4 millimeters, and a height of about 2 millimeters.

The organic indicating material may be placed 120 on the first cured polymeric material. In some embodiments, the organic indicating material may be placed 120 in the center of the first cured polymeric material. In other embodiments, the organic indicating material may be placed 120 off center of the first cured polymeric material.

A chemical reactant may optionally be placed 125 adjacent to a surface of the organic indicating material. In some embodiments, the chemical reactant may catalyze an exothermic reaction that heats the organic indicating material. In other embodiments, the chemical reactant may react with the target material and undergo an exothermic reaction which will then heat the organic indicating material. In some embodiments, the chemical reactant may be acetic acid, ammonium hydroxide, calcium hydroxide, carbonic acid, hydrochloric acid, hydrogen peroxide, magnesium, nitric acid, oxygen gas, palladium, platinum, potassium hydroxide, salts, sodium hydroxide, sulphuric acid, titanium dioxide, or any combination thereof. In some embodiments, the chemical reactant may have a fluorescent tag.

The second curable polymeric material may be applied 130. In some embodiments, the second curable polymeric material may be applied 130 by pouring the material, adding the material dropwise, dispensing the material, or the like.

The second curable polymeric material may be cured 135. In some embodiments, the second curable polymeric material may be cured 135 by chemical additives, ultraviolet radiation, electron beam, heat, or any combination thereof. In other embodiments, the curing 135 of the second curable polymeric material may be performed via multiple steps to achieve various levels of curing of the second curable polymeric material. In further embodiments, the curing 135 of the second curable polymeric material may be step-curing, ramp curing, single intensity curing, or any other method of curing. In some embodiments, the second curable polymeric material may be cured 135 in the presence of oxygen. In other embodiments, the second curable polymeric material may be cured 135 in the absence of oxygen. In other embodiments, the second curable polymeric material may be cured 135 at a temperature of about 20° C. to about 350° C. For example, the material may be cured 135 at a temperature of about 20° C., about 40° C., about 60° C., about 80° C., about 100° C., about 120° C., about 140° C., about 160° C., about 180° C., about 200° C., about 250° C., about 300° C., about 350° C., or in a range between any of these values (including endpoints). In some embodiments, the second curable polymeric material may be cured 135 to a flexible state.

In some embodiments, the organic indicating material may form a visual indicator in the solid polymeric matrix when diffused into the solid polymeric matrix. The visual indicator may indicate the extent of diffusion and thus the thermal, chemical, or biological load on the sensor. In some embodiments, the visual indicator may provide a measurement of the thermal, chemical, or biological load. In some embodiments, an index may be placed 140 on the solid polymeric matrix adjacent to the organic indicating material in order to measure the visual indicator. The index may include words and/or line markings. In some embodiments, the line markings may indicate a distance used to measure the extent of diffusion of the organic indicating material. In other embodiments, the words "safe" and "unsafe" may be used above line markings. In further embodiments, the index may be one or more concentric rings surrounding the organic indicating material. The concentric rings may be used to measure the distance that the organic indicating material diffuses into the solid polymeric matrix. The index may be an opaque covering that acts as a binary indicator of the thermal load when the organic indicating material diffuses beyond the index. The index may be an opaque and colored shape in a bottom of the sensor that may become concealed by the organic indicating material after the organic indicating material diffuses into the solid polymeric matrix. In some embodiments, a plurality of indices may be placed 140 on the solid polymeric matrix in order to measure the visual indicator.

Figure 2:
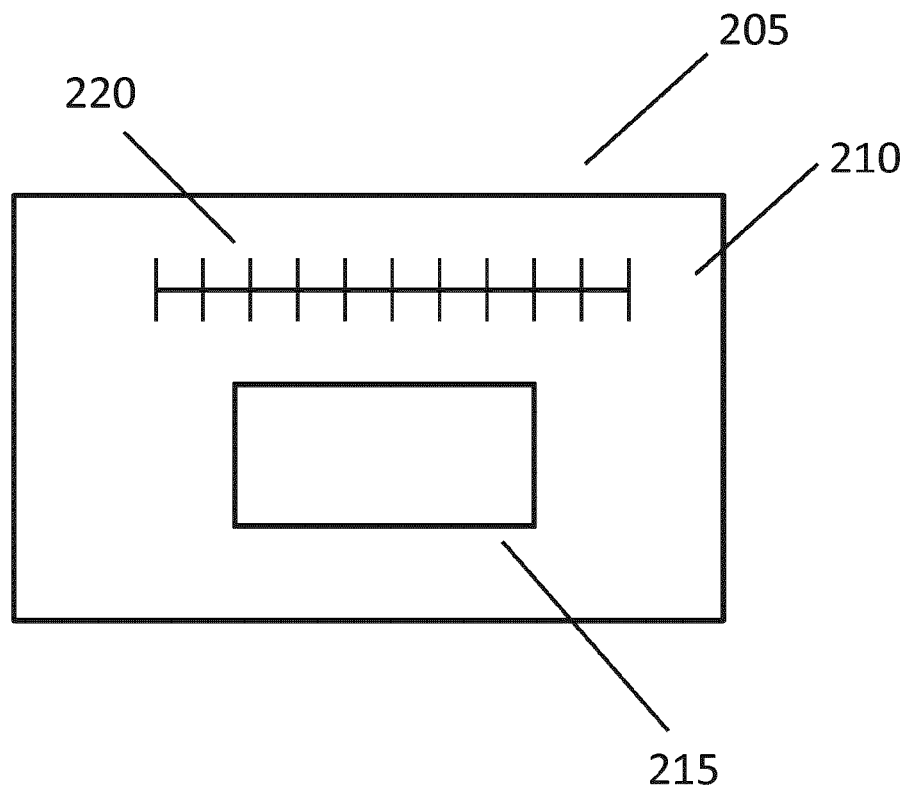
FIG. 2 depicts a cross-sectional illustration of a thermal load sensor according to an embodiment.

A thermal load sensor 205 for detecting thermal load is illustrated in FIG. 2. In some embodiments, the thermal load sensor 205 may have a solid polymeric matrix 210 and at least one organic indicating material 215. In some embodiments, the thermal load sensor 205 may be in the shape of a cube, a cuboid, a square-based pyramid, a triangular-based pyramid, a triangular prism, a hexagonal prism, a cone, a sphere, a cylinder, or a combination thereof.

In some embodiments, the solid polymeric matrix 210 may be a hydrophobic elastomeric material. In other embodiments, the solid polymeric matrix 210 may be polycarbonate, an acrylate polymer, polyurethane, a siloxane-based polymer, and a co-polymer of any of the foregoing. In further embodiments, the solid polymeric matrix 210 may be polydimethylsiloxane. In an embodiment, the solid polymeric matrix 210 may be polydimethylsiloxane in a flexible state.

In some embodiments, the organic indicating material 215 may be encapsulated within the solid polymeric matrix 210. In some embodiments, the organic indicating material 215 may be a hydrophobic material that undergoes a phase transition from a solid to a liquid at the phase transition temperature. In some embodiments, the organic indicating material 215 may have a carbon chain with at least 2 carbon atoms. In other embodiments, the organic indicating material 215 may have a carbon chain with at least 2 carbon atoms to at least 100 carbon atoms. For example, the organic indicating material 215 may have at least 2 carbon atoms, at least 3 carbon atoms, at least 4 carbon atoms, at least 5 carbon atoms, at least 6 carbon atoms, at least 7 carbon atoms, at least 8 carbon atoms, at least 9 carbon atoms, at least 10 carbon atoms, at least 15 carbon atoms, at least 20 carbon atoms, at least 50 carbon atoms, at least 100 carbon atoms, or any range between these values. In further embodiments, the organic indicating material 215 may be a paraffin having at least 2 carbon atoms to at least 100 carbon atoms. In some embodiments, the organic indicating material may be a paraffin having at least 9 carbon atoms. In other embodiments, the organic indicating material 215 may be a paraffin wax. In some embodiments, the thermal load sensor 205 may include a plurality of organic indicating materials 215.

In some embodiments, the organic indicating material 215 may be in the shape of a cube, a cuboid, a square-based pyramid, a triangular-based pyramid, a triangular prism, a hexagonal prism, a cone, a sphere, a cylinder, and combinations thereof. In other embodiments, the organic indicating material 215 may be a cylinder. In other embodiments, the cylinder may have a cross-sectional diameter of about 1 millimeter to about 30 millimeters. For example, the cylinder may have a cross-sectional diameter of about 1 millimeter, about 2 millimeters, about 3 millimeters, about 4 millimeters, about 5 millimeters, about 6 millimeters, about 7 millimeters, about 8 millimeters, about 9 millimeters, about 10 millimeters, about 20 millimeters, about 30 millimeters, or a range between any of these values (including endpoints). In other embodiments, the cylinder may have a height of about 0.5 millimeters to about 20 millimeters. For example, the cylinder may have a height of about 0.5 millimeters, about 1 millimeter, about 2 millimeters, about 3 millimeters, about 4 millimeters, about 5 millimeters, about 10 millimeters, about 20 millimeters, or a range between any of these values (including endpoints). In one embodiment, the cylinder may have a diameter of about 1 millimeter to about 10 millimeters and a height of about 0.5 millimeters to about 5 millimeters. In a particular embodiment, the cylinder may have a diameter of about 4 mm, and a height of about 2 mm.

In some embodiments, the organic indicating material 215 may be located in the center of the solid polymeric matrix 210. In other embodiments, the organic indicating material 215 may not be centered with respect to the solid polymeric matrix 210.

In some embodiments, the organic indicating material 215 may diffuse into the solid polymeric matrix 210 at a phase transition temperature of the organic indicating material 215. The extent of the diffusion may indicate a thermal load on the sensor 205. In some embodiments, the thermal load may be indicated as a change in the solid polymeric matrix 210 from transparent to opaque. Alternatively, the thermal load may be indicated as any change in color of the solid polymeric matrix 210. The change in color may be any color within the visible spectrum and may change to a lighter or darker shade based on the diffusion of the organic indicating material 215.

In some embodiments, the thermal load may include an exposure time. In other embodiments, the thermal load may include an exposure temperature. In further embodiments, the thermal load may include both an exposure time and an exposure temperature.

In some embodiments, the thermal load sensor 205 may include an index 220 on the solid polymeric matrix 210 adjacent to the organic indicating material 215 in order to measure the visual indicator formed by the organic indicating material 215. The index 220 may also include words and/or markings. The markings, can for example, be line markings. In some embodiments, the index may include at least a first marking and a second marking. In some embodiments, the markings may indicate a distance that measures the extent of diffusion of the organic indicating material. In other embodiments, the words "safe" and "unsafe" may be used above line markings. Other words or symbols may also be used to indicate the thermal load, or to indicate a chemical or biological load for sensors that detect such loads as will be described below, and can for example be "prolonged exposure to load", "moderate exposure to load" and "no exposure to load", or symbols along the index that represent exposure to the load at varying temperatures of the surrounding, varying concentrations of contaminants, varying periods of exposure to the load, or combinations thereof. In further embodiments, the index may be one or more concentric rings surrounding the organic indicating material. The concentric rings may be used to measure the distance that the organic indicating material diffuses into the solid polymeric matrix. The index may be an opaque covering that acts as a binary indicator of the thermal load when the organic indicating material diffuses beyond the index. The index may be an opaque and colored shape in a bottom of the sensor that may become concealed by the organic indicating material after the organic indicating material diffuses into the solid polymeric matrix. In some embodiments, the thermal load sensor 205 may include a plurality of indices on the solid polymeric matrix 210 in order to measure the visual indicator.

The thermal load sensor may be used for detecting a thermal load on an article by providing the sensor on a surface of the article or on a surface of a container in which the article resides, and determining the thermal load from the sensor based on an amount of diffusion of the organic indicating material 215 into the solid polymeric matrix 210. The article can be any item that is sensitive to the thermal load and can, for example, be a food item, a pharmaceutical drug, or an electronic device.

Figure 3:
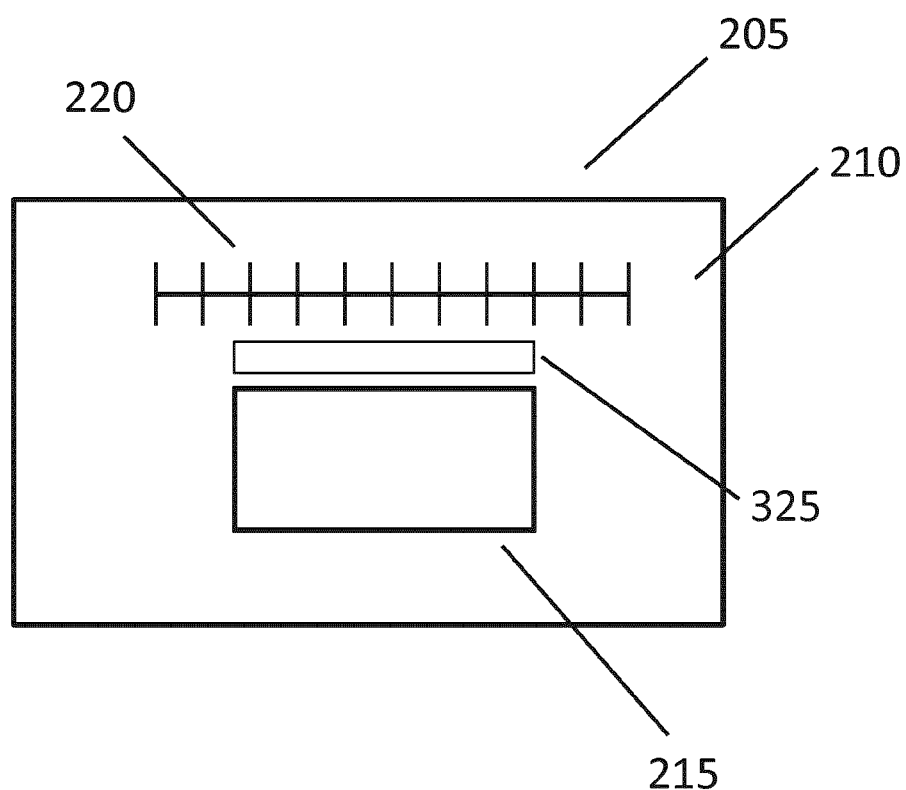
FIG. 3 depicts a cross-sectional illustration of a chemical or biological load sensor according to an embodiment.

A chemical or biological load sensor 205 is illustrated in FIG. 3. FIG. 3 incorporates all features of FIG. 2 with the addition of a chemical reactant and reservoir 325 for the chemical reactant.

In some embodiments, the chemical or biological load sensor 205 may include a chemical reactant positioned adjacent to a surface of the organic indicating material 215. In some embodiments, the chemical or biological load sensor 205 may include a reservoir 325 for the chemical reactant within the solid polymeric matrix 210 and adjacent to the organic indicating material 215. In some embodiments, the chemical or biological load sensor 205 may include a plurality of reservoirs 325 for the chemical reactant within the solid polymeric matrix 310 and adjacent to the plurality of organic indicating materials 215. In some embodiments, the chemical reactant may catalyze the exothermic reaction that heats the organic indicating material 215. In other embodiments, the chemical reactant may react with the target material and undergo the exothermic reaction which will then heat the organic indicating material.

In some embodiments, the target material may be a pesticide, a hormone, a microorganism, a dye composition, a polymer, a hydrogen gas, an acid, a base, a volatile organic compound, or any combination thereof. The acid may include, for example, acetic acid, benzoic acid, carbonic acid, formic acid, hydrochloric acid, hydrogen sulfide, nitric acid, phosphoric acid, sulfuric acid or any combination thereof. The base, for example, may include ammonium hydroxide, calcium hydroxide, potassium hydroxide, sodium hydroxide, or any combination thereof.

In some embodiments, the chemical reactant may be acetic acid, ammonium hydroxide, calcium hydroxide, carbonic acid, hydrochloric acid, hydrogen peroxide, magnesium, nitric acid, oxygen gas, palladium, platinum, potassium hydroxide, salts, sodium hydroxide, sulphuric acid, titanium dioxide, or any combination thereof.

In some embodiments, the chemical or biological load may include time of exposure to the target material, concentration of the target material, type of target material, or any combination thereof.

The chemical or biological load sensor 205 may be used for detecting chemical or biological target materials by providing the sensor in an environment suspected of having those target materials, and determining a chemical or biological load from the sensor based on an amount of diffusion of the organic indicating material 215 into the solid polymeric matrix 210.

The sensors above may be incorporated into an article of manufacture. In some embodiments, the article of manufacture may include a sensor 205 such as those shown in FIGS. 2 and 3.

In some embodiments, the sensor 205 may be a thermal load sensor 205. In some embodiments, the thermal load may include time of exposure. In other embodiments, the thermal load may include temperature of exposure. In further embodiments, the thermal load may include time of exposure and temperature of exposure.

In some embodiments, the sensor 205 may be a chemical or biological load sensor 205. In some embodiments, the chemical or biological load may include time of exposure to a target material, concentration of the target material, type of target material, or any combination thereof. In some embodiments, the sensor 205 may be exposed to a target material. In some embodiments, the organic indicating material 215 may react with the target material and result in an exothermic reaction that heats the organic indicating material 215 to the phase transition temperature.

In some embodiments, the target material may be a pesticide, a hormone, a microorganism, a dye composition, a polymer, a hydrogen gas, an acid, a base, a volatile organic compound, or any combination thereof. The acid may include, for example, acetic acid, benzoic acid, carbonic acid, formic acid, hydrochloric acid, hydrogen sulfide, nitric acid, phosphoric acid, sulfuric acid, or any combination thereof. The base, for example, may include ammonium hydroxide, calcium hydroxide, potassium hydroxide, sodium hydroxide, or any combination thereof.

In some embodiments, the article of manufacture may optionally include a chemical reactant. In some embodiments, the chemical reactant may be adjacent to the formed organic indicating material 215. In some embodiments, the chemical reactant may catalyze the exothermic reaction that heats the organic indicating material. In other embodiments, the chemical reactant may undergo an exothermic reaction with the target material after exposure of the sensor to the target material and result in the heating of the organic indicating material 215 to the phase transition temperature. In further embodiments, the article of manufacture may include a visual indicator in the solid polymeric matrix 210 formed by the organic indicating material 215. The visual indicator may indicate the extent of diffusion and thus the target load on the sensor 205.

EXAMPLES

Example 1: A Method of Making a Thermal Load Sensor

A thermal load sensor was made in a cylindrical empty container. A 5 millimeter thick layer of uncured polydimethylsiloxane (PDMS) pre-polymer having a monomer and a cross-linker was poured into the container. The uncured PDMS was cured to a gel at the gel point temperature (90° C.). Paraffin wax was used as the organic indicating material. The paraffin wax was thermoformed into four cylinders with a diameter of 4 millimeters and a height of 2 millimeters. The four paraffin wax cylinders were placed in the center of the cured PDMS and were spaced equally apart. An additional 5 millimeter layer of uncured PDMS was poured over the paraffin wax cylinders to completely cover the paraffin wax cylinders. The uncured PDMS was cured under similar conditions as the previous layer of PDMS. A surface of the thermal load sensor was imprinted with visual markers for thermal load measurement. The thermal load sensor having the paraffin disk surrounded by the PDMS encapsulant were cut removed from the container. The thermal load sensor was placed on an 80° C. hot plate for 30 minutes. The paraffin wax diffused into the PDMS matrix and created cloudy rings that were equally spaced apart in the PDMS surrounding the paraffin wax. The cloudy rings form concentric rings around the location of the paraffin wax. It was observed that as the exposure time of the sensor to the heat increased, the extent of diffusion of the paraffin wax increased and hence the number of concentric rings also increased. The visual markers were line markings extending outwardly from the location of the paraffin wax, which were calibrated to indicate the time of exposure based on the extent of diffusion of the paraffin wax. Accordingly, the thermal load sensor can detect a thermal load, such as time of exposure to elevated temperatures as described in this Example.

Example 2: A Sensor for Detecting Biological Target Materials

A sensor will be used to detect a biological load. The sensor will have an acrylate polymer matrix that encapsulates a paraffin cylinder and a reservoir of hydrogen peroxide positioned adjacent to the paraffin cylinder. An index will be included adjacent to the paraffin cylinder on the acrylate polymer matrix. The index will have two line markings indicating the risk of yeast contamination, one line will have the word 'low risk' above it, and the other line will be further from the paraffin cylinder and will have the word 'high risk' above it. The sensor will be designed to detect yeast in the surrounding environment. The sensor will be attached to a box of apples. When yeast is present in the environment, the hydrogen peroxide will react with the yeast and release heat. The heat will melt the paraffin wax, resulting in the paraffin wax diffusing into the acrylate polymer matrix. The index will be used to determine the extent of diffusion of the paraffin wax to determine if the amount of yeast detected in the surrounding environment has reached levels that would contaminate the apples.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as “open” terms (for example, the term “including” should be interpreted as “including but not limited to,” the term “having” should be interpreted as “having at least,” the term “includes” should be interpreted as “includes but is not limited to,” et cetera). While various compositions, methods, and devices are described in terms of “comprising” various components or steps (interpreted as meaning “including, but not limited to”), the compositions, methods, and devices can also “consist essentially of” or “consist of” the various components and steps, and such terminology should be interpreted as defining essentially closed-member groups. It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases “at least one” and “one or more” to introduce claim recitations. However, the use of such phrases should not be construed to imply that the introduction of a claim recitation by the indefinite articles “a” or “an” limits any particular claim containing such introduced claim recitation to embodiments containing only one such recitation, even when the same claim includes the introductory phrases “one or more” or “at least one” and indefinite articles such as “a” or “an” (for example, “a” and/or “an” should be interpreted to mean “at least one” or “one or more”); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of “two recitations,” without other modifiers, means at least two recitations, or two or more recitations). Furthermore, in those instances where a convention analogous to “at least one of A, B, and C, et cetera” is used, in general, such a construction is intended in the sense one having skill in the art would understand the convention (for example, “a system having at least one of A, B, and C” would include but not be limited to systems that have A alone, B alone, C alone, A and B together, A and C together, B and C together, and/or A, B, and C together, et cetera). In those instances where a convention analogous to “at least one of A, B, or C, et cetera” is used, in general, such a construction is intended in the sense one having skill in the art would understand the convention (for example, “a system having at least one of A, B, or C” would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase “A or B” will be understood to include the possibilities of “A” or “B” or “A and B.”

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof.

Any listed range can be easily recognized as sufficiently describing and enabling the same range being broken down into at least equal halves, thirds, quarters, fifths, tenths, et cetera As a non-limiting example, each range discussed herein can be readily broken down into a lower third, middle third and upper third, et cetera As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A method of making a sensor, the method comprising:
encapsulating at least one organic indicating material in a solid polymeric matrix, wherein the at least one organic indicating material is configured to diffuse into the solid polymeric matrix when contacted with a target material that triggers an exothermic reaction to heat the at least one organic indicating material to a phase transition temperature, and wherein an extent of diffusion indicates a chemical or biological load on the sensor.

2. A method of making a sensor, the method comprising:
encapsulating at least one organic indicating material in a solid polymeric matrix, wherein the at least one organic indicating material is configured to diffuse into the solid polymeric matrix at a phase transition temperature of the at least one organic indicating material, wherein an extent of diffusion indicates a load on the sensor and, wherein the encapsulating comprises:
providing a first curable polymeric material into a container;
curing the first curable polymeric material to form a first cured polymeric material;
forming the at least one organic indicating material into a shape smaller than the first cured polymeric material;
placing the at least one organic indicating material on the first cured polymeric material;
applying a second curable polymeric material on the at least one organic indicating material and the first cured polymeric material so as to encapsulate the at least one organic indicating material; and
curing the second curable polymeric material to form a second cured polymeric material.

3. The method of claim 1, wherein the at least one organic indicating material comprises a hydrophobic material that undergoes a phase transition from a solid to a liquid at the phase transition temperature.

4. The method of claim 1, wherein the at least one organic indicating material is a paraffin having at least 9 carbon atoms.

5. The method of claim 2, wherein at least one of the first curable polymeric material and the second curable polymeric material is a hydrophobic elastomeric material.

6. The method of claim 2, wherein at least one of the first curable polymeric material and the second curable polymeric material is polydimethylsiloxane, and wherein curing at least one of the first curable polymeric material and the second curable polymeric material comprises curing the polydimethylsiloxane to a flexible state.

7. The method of claim 1, wherein the encapsulating further comprises placing a chemical reactant adjacent to a surface of the at least one organic indicating material.

8. The method of claim 7, wherein the chemical reactant is configured to catalyze the exothermic reaction.

9. The method of claim 7, wherein the chemical reactant is configured to react with the target material to result in the exothermic reaction.

10. The method of claim 7, wherein the chemical reactant has a fluorescent tag.

11. A sensor, comprising:
a solid polymeric matrix, and at least one organic indicating material encapsulated within the solid polymeric matrix,
wherein the at least one organic indicating material is configured to diffuse into the solid polymeric matrix when contacted with a target material that triggers an exothermic reaction to heat the at least one organic indicating material to a phase transition temperature, and wherein an extent of diffusion indicates a chemical or biological load on the sensor.

12. The sensor of claim 11, wherein the at least one organic indicating material comprises a hydrophobic material that is configured to undergo a phase transition from a solid to a liquid at the phase transition temperature, wherein the phase transition temperature is about 30 degrees Celsius to about 300 degrees Celsius, and wherein the extent of diffusion indicates a thermal load on the sensor.

13. The sensor of claim 11, wherein the at least one organic indicating material is configured to form a visual indicator in the solid polymeric matrix when diffused into the solid polymeric matrix, and the visual indicator is configured to indicate the extent of diffusion and thus a thermal load on the sensor, and
wherein the sensor further comprises an index on the solid polymeric matrix adjacent to the at least one organic indicating material, and wherein the index provides a measurement of the thermal load based on the visual indicator.

14. The sensor of claim 11, wherein the solid polymeric matrix is polydimethylsiloxane in a flexible state.

15. The sensor of claim 11, further comprising a chemical reactant positioned adjacent to a surface of the at least one organic indicating material.

16. The sensor of claim 15, wherein the chemical reactant is configured to catalyze the exothermic reaction or react with the target material to result in the exothermic reaction.

17. The sensor of claim 15, further comprising a reservoir for the chemical reactant that is positioned within a cured polymeric material and adjacent to the surface of the at least one organic indicating material.

18. A sensor prepared according to the method of claim 1.

19. A sensor prepared according to the method of claim 2.

20. The method of claim 2, wherein the at least one organic indicating material is a paraffin having at least 9 carbon atoms.

* * * * *